United States Patent
Bashir et al.

(10) Patent No.: US 10,251,924 B2
(45) Date of Patent: Apr. 9, 2019

(54) COMPOSITIONS CONTAINING MYRISTICA FRAGRANS

(71) Applicant: Northern Innovations Holding Corp, Oakville (CA)

(72) Inventors: Raza Bashir, Oakville (CA); Philip Apong, Oakville (CA); Anna Lytvyn, Oakville (CA)

(73) Assignee: Northern Innovations Holding Corp, Oakville, Ontario (CA)

( * ) Notice: Subject to any disclaimer, the term of this patent is extended or adjusted under 35 U.S.C. 154(b) by 74 days.

(21) Appl. No.: 14/036,097

(22) Filed: Sep. 25, 2013

(65) Prior Publication Data
US 2015/0086660 A1    Mar. 26, 2015

(51) Int. Cl.
| | |
|---|---|
| *A61K 36/537* | (2006.01) |
| *A61K 36/185* | (2006.01) |
| *A61K 36/03* | (2006.01) |
| *A61K 36/74* | (2006.01) |

(52) U.S. Cl.
CPC ............ *A61K 36/537* (2013.01); *A61K 36/03* (2013.01); *A61K 36/185* (2013.01); *A61K 36/74* (2013.01)

(58) Field of Classification Search
None
See application file for complete search history.

(56) References Cited

U.S. PATENT DOCUMENTS

| | | | | | |
|---|---|---|---|---|---|
| 4,670,463 | A  * | 6/1987  | Warren | ................ | A61K 31/335 424/47 |
| 6,488,955 | B1 * | 12/2002 | Decombaz | .............. | A23L 1/095 424/439 |
| 2008/0020071 | A1 * | 1/2008  | Diaz | ...................... | A61K 36/00 424/752 |
| 2008/0233245 | A1 * | 9/2008  | White | ..................... | A23L 1/296 426/73 |
| 2008/0249063 | A1 * | 10/2008 | Heuer | .................... | A61K 31/05 514/54 |
| 2009/0274777 | A1 * | 11/2009 | Shimoda | ................... | A23F 5/02 424/725 |
| 2012/0052137 | A1 * | 3/2012  | Shirazi | ................... | A61K 36/45 424/729 |
| 2012/0083525 | A1 * | 4/2012  | Oh | ....................... | A61K 31/341 514/461 |

OTHER PUBLICATIONS 2016 https://en.wikipedia.org/wiki/Salvia_officinalis.*
2016 http://supplementpolice.com/ecklonia-cava/.*
2016 https://en.wikipedia.org/wiki/Pausinystalia_johimbe.*

* cited by examiner

*Primary Examiner* — Terry A McKelvey
*Assistant Examiner* — Catheryne Chen

(57) ABSTRACT

Compositions as nutritional supplements comprising extracts of *Myristica fragrans* for improving exercise performance and for promoting weight loss are disclosed. The compositions may contain, and be standardized to, myristicin and may be administered prior to physical exercise.

21 Claims, No Drawings

COMPOSITIONS CONTAINING MYRISTICA FRAGRANS

FIELD OF THE INVENTION

The present invention relates generally to compositions comprising extracts of *Myristica fragrans*. More specifically, the invention relates to methods of using extracts comprising *Myristica fragrans* for improving exercise performance and for promoting weight loss or maintenance.

BACKGROUND OF THE INVENTION

Weight loss is achieved with a net increase in calories spent relative to calories consumed. Increased caloric spend is primarily achieved through increased physical activity, while decreased caloric consumption is primarily achieved by reducing food consumption. Reduced energy intake (i.e. food) combined with increased energy expenditure is an effective weight-loss strategy. Each of these strategies will independently contribute to weight loss; however, each may also be associated with increased stress or anxiety, which is not conducive to weight loss. Dieting, in particular, has been associated with depressed mood and, in some such cases, mood-improving agents (such as antidepressants) are useful as weight control agents.

Weight control products seek to aid weight loss (or weight maintenance) and operate through one or more modes such as appetite suppression, increasing thermogenesis, inhibiting lipogenesis, and by reducing caloric input by blocking absorption of various macromolecules such as either fats or carbohydrates. Various dietary supplements may be used to aid or support weight loss. Dietary supplements may be used with the primary goal of directly promoting appetite suppression, increasing thermogenesis, inhibiting lipogenesis, or by blocking carbohydrate or fat absorption. Alternatively, dietary supplements may be employed to improve physical exercise as a less direct means to control body weight by way of increasing calories expended.

A common ingredient used in products for improving exercise performance and for promoting weight loss or maintenance is caffeine. However, the use of caffeine is sometimes associated with negative effects despite the benefits. Exercise as well, despite potential profound benefits does carry some possible negative effects such as injury, (temporarily) increased fatigue, and (temporarily) increased stress. The potential negative effects of dieting and/or exercise in terms of stress and mood may be increased by caffeine use.

Accordingly, there is a need for nutritional supplements that improve exercise performance and promote weight loss or maintenance. Particularly in supplements that contain caffeine.

SUMMARY OF THE INVENTION

The disclosed dietary supplements and methods of administering the same can advantageously be used to individuals who desire increased energy, increased thermogenic effects, and/or improved mental focus and mood, particularly for improving exercise performance or promoting weight loss or maintenance.

In an embodiment of the invention, there are provided compositions comprising extracts of *Myristica fragrans*. In some aspects, the extracts contain myristicin.

In another embodiment, there are provided methods of administering compositions comprising extracts of *Myristica fragrans* for improving exercise performance. In some aspects, the extracts contain myristicin.

In another embodiment, there are provided methods of administering compositions comprising extracts of *Myristica fragrans* for promoting weight loss. In some aspects, the extracts contain myristicin.

In another embodiment, there are provided compositions that contain myristicin. In some aspects, the myristicin is extracted from a natural source, preferably *Myristica fragrans*. In other aspects, the myristicin may be synthetically-derived.

DETAILED DESCRIPTION OF THE EMBODIMENTS

A used herein, the terms 'composition' or 'nutritional composition' includes dietary supplements, diet supplements, nutritional supplements, supplemental compositions and supplemental dietary compositions or those similarly envisioned and termed compositions not belonging to the conventional definition of pharmaceutical interventions as is known in the art. Furthermore, 'nutritional compositions' as disclosed herein belong to category of compositions having at least one physiological function when administered to a mammal by conventional routes of administration.

Alternatively, formulations and nutritional compositions belonging to the present invention may be considered to be nutraceuticals. As used herein, the term 'nutraceutical' is recognized and used in the art to describe a specific chemical compound or combination of compounds found in, organic matter for example, which may prevent, ameliorate or otherwise confer benefits against an undesirable condition. As is known in the art, the term 'nutraceutical' is used to refer any substance that is a food, a part of food, or an extract or derivative of food which is suitable for consumption by an individual and providing physiological benefit which may be medical or health-related. Furthermore, the term has been used to refer to a product isolated, extracted or purified from foods or naturally-derived material suitable for consumption by an individual and usually sold in medicinal forms, such as caplets, tablet, capsules, soft gel capsules, gel-caps and the like, not associated with food.

As used herein, the term "promoting weight loss" and related terms are used to refer to any action or effect, directly or indirectly, conducive to an overall reduction in total body weight of an individual. As used herein, the term "promoting weight loss" and related terms are also understood to include body weight maintenance, particularly in cases where an individual may wish to reduce body fat specifically, while maintaining muscle or minimizing muscle loss while reducing body fat, which, in some aspects may not manifest as a reduction in total body weight.

As used herein, the terms "thermogenesis", "thermogenic effect", and related terms are understood to relate to the process of heat production in or by the body, particularly increased heat production by or in the body. It is also understood that thermogenesis may be increased by a number of mechanisms including, but not limited to diet-induced thermogenesis, exercise-induced thermogenesis, and non-exercise-associated thermogenesis. As used herein, a "thermogenic substance/supplement" is understood to mean any substance, which when ingested by a subject increases thermogenesis. This is understood to be associated with any or all of increased heat production by the body, increased energy expenditure, and increased metabolic rate.

"Focus" as used herein, refers to mental or cognitive functions such as attention, concentration, and memory. It is understood that mental/cognitive functions may be related to, and impacted by, physical energy and stress. Focus may also be related to mood, anxiety, and sense of well-being.

"Energy" as used herein, refers to actual or perceived ability to exert physical effort and perform work (such as exercise). It is understood that energy also relates to mental energy and may be impacted by focus as defined above.

The inventors believe that *Myristica fragrans*, particularly *Myristica fragrans* extract would be beneficial in compositions for improving exercise performance and for promoting weight loss or maintenance, particularly in compositions containing caffeine since many nutritional supplements used for improving exercise performance and for promoting weight loss or maintenance contain caffeine for providing energy and mental focus. Such use of caffeine is primarily due to its action as a central nervous system stimulant but it may also spare glycogen by promoting the utilization of fat for energy. Despite its widespread use, there are some drawbacks associated with the use, particularly chronic use, of caffeine such as tolerance, sensitivity, and side effects that may be associated with caffeine consumption including 'jolt and crash', increased cortisol, insomnia, and jitteriness. It is known that habitual caffeine use can lead to tolerance whereby the stimulant effects of an acute dose of caffeine are diminished. Tolerance—real or perceived—to some of the effects of caffeine with regular use develops quickly, typically from hours to days and is associated with an increase in adenosine receptor activity. This tolerance is related to withdrawal symptoms. However, despite tolerance, benefits from regular caffeine consumption persist when used in the context of pre-workout and weight loss supplementation. Despite any unwanted effects, caffeine continues to be regular component of daily dietary consumption and a popular pre-workout and weight loss aid for many individuals. In particular, the inventors believe that *Myristica fragrans* or some of its components would be useful in terms of providing or improving the increased energy, the thermogenic effect, or the increased focus perceived or experienced by the individual consuming the composition, particularly in combination with caffeine. In particular, *Myristica fragrans* or some of its components may be useful for allowing the use of caffeine or increased dosages of caffeine where sensitivity or negative effects would otherwise discourage such use.

Nutmeg is considered the dried seeds of *Myristica fragrans*, an aromatic evergreen tree. Nutmeg has traditional use as a spice and for treating stomach cramps, muscle spasms, reduced appetite, diarrhea, and rheumatism. In high doses, there have been reported psychotropic effects.

*Myristica fragrans* or some of its actives have been associated with hepatoprotective effects, anti-diarrheal activity, antimicrobial activity, antioxidant activity, and anti-inflammatory activity. According to various animal studies (mouse and rat), myristicin has been shown to increase anxiety and counteract anxiolytic drugs, although this effect may be dose-dependent with some doses in some studies showing the opposite effect. Myristicin is a component of *Myristica fragrans* (nutmeg) and is a main component of nutmeg essential oil. Other components of *Myristica fragrans* include myristic acid, elemicin, safrole, eugenol, palmitic acid, oleic acid, lauric acid, and other acids.

The compositions of the present invention contain *Myristica fragrans*. *Myristica fragrans* may be provided as whole, fresh or dried, *Myristica fragrans* plant, or any part thereof, such as leaves, flowers, fruit, seeds, stems, or roots. In preferred aspects, the plant part used is the seed. Preferably, the *Myristica fragrans* is in the form of an extract. Extraction techniques suitable for use with plants and plant material are well known in the art. It is herein understood that the goal of extraction is to concentrate or separate soluble plant metabolites, including desired active components, from structural plant matter, or otherwise unwanted plant matter. The final form of an extract may be liquid (aqueous or oil), semi-solid, or powdered. The *Myristica fragrans* extract may be standardized to one or more specific components of the extract or may be expressed as an extract ratio, the preferred ratio being from about 4:1 to about 10:1, most preferably about 5:1. Basic extracts may contain a complex mixture of many plant metabolites, such as alkaloids, glycosides, terpenoids, flavonoids and lignans. The preferred extract is an aqueous *Myristica fragrans* extract, most preferably, an aqueous seed extract. Other suitable forms of extracts include alcoholic extracts such as ethanolic or methanolic. Additionally suitable extraction methods are hydroalcoholic extracts using solvent mixtures of alcohol and water of various portions. Distillation may also be used to extract essential oil. Such extracts may be standardized to at least one principal component.

In preferred embodiments, the *Myristica fragrans* provides myristicin. In such embodiments, the amount of myristicin per serving of the composition will be from about 10 micrograms to about 10 milligrams.

Preferably, the amount of myristicin per serving of the composition will be from about 50 micrograms to about 5 milligrams. More preferably, the amount of myristicin per serving of the composition will be from about 70 micrograms to about 3 milligrams; other preferred compositions comprises myristicin in an amount from about 50 to about 150 micrograms, for example, 10, 25, 50, 75, 100, 125 150, 175, 200, 250, 300, 400, 500, 600, 700, 800 or 900 micrograms, or 1, 2, 2.5, 3, 5, 7.5 or 10 mg. Most preferably, the amount of myristicin per serving of the composition will be about 100 micrograms.

The inventors formulated and tested multiple compositions containing *Myristica fragrans* as well as other ingredients useful for improving exercise performance and for promoting weight loss. In preferred embodiments, the compositions and methods of using the compositions will contain *Myristica fragrans* and a source of caffeine. The preferred form of caffeine is caffeine anhydrous; however, the source of caffeine may be other known sources such as Coffea Arabica, Coffea canephora, Camellia sinensis, *Ilex paraguariensis, Paullinia cupana, Theobroma cacao*, and kola nut, provided the required amount of caffeine is provided. The amount of caffeine per serving of the composition is from about 50 to 300 mg of caffeine. More preferably, the amount of caffeine per serving of the composition is from about 80 to 250 mg, or about 100 to 250 mg, for example, 50, 75, 80, 100, 120, 135, 150, 180, 200, 225, 250, 275 or 300 mg. Most preferably, the amount of caffeine per serving of the composition is about 135 mg.

In some embodiments, compositions containing *Myristica fragrans* (with or without caffeine) may also contain additional ingredients, including but not limited to: Raspberry ketone, *Salvia officinalis, Ecklonia cava, Pausinystalia yohimbe* and Green coffee bean (*Coffea canephora/Coffea robusta*). Preferred ingredients are *Ecklonia cava* and *Salvia officinalis*.

Preferred embodiments of the invention, for example, may comprise raspberry ketone in an amount from about 5 to 200 mg; about 10 to 150 mg; about 25 to 125 mg; about 40 to 100 mg; for example, about 5, 10, 25, 30, 40, 45, 50, 55, 60, 65, 75, 80 or 100 mg; and most preferably about 50 mg; *Salvia officinalis* in an amount from about 5 to 200 mg;

about 10 to 150 mg; about 25 to 125 mg; about 40 to 100 mg; for example, about 5, 10, 25, 30, 40, 45, 50, 55, 60, 65, 75, 80 or 100 mg; and most preferably about 50 mg; *Ecklonia cava* in an amount from about 3 to 100 mg; about 5 to 75 mg; about 7.5 to 50 mg; about 10 to 40 mg; for example, about 3, 5, 7.5, 10, 12.5, 15, 17.5, 18, 20, 22.5, 25, 27.5, 30, 35, 40, 45 or 50 mg; and most preferably about 18 mg; *Pausinystalia yohimbe* in an amount from about 100 microgram to 50 mg; about 1 to 40 mg; about 2.5 to 30 mg; about 5 to 20 mg; for example, about 100 micrograms, 250 micrograms, 500 micrograms, 1 mg, 2.5, 4, 5, 7.5, 8.5, 10, 12.5, 15, 20, 25, 30, 35, 40, 45, or 50 mg; and most preferably about 8.5 mg; and Green coffee bean (*Coffea canephora/Coffea robusta*) in an amount about 50 mg to 1 g; about 75 to 800 mg; about 100 to 750 mg; about 200 to 600 mg; about 300 to 500 mg, for example, about 50, 75, 100, 150, 200, 250, 300, 350, 400, 450, 500, 600, 700, 750, 800, 900 mg or 1 g; and most preferably about 400 mg.

EXAMPLES

*Myristica fragrans* and *Salvia officinalis* were each separately tested in individuals and found to have an effect of enhancing perceived focus. Combination with caffeine appeared to amplify the focus-enhancing benefits as well as providing perceived energy and thermogenic effect. The inventors tested multiple combinations and dosages to produce compositions comprising *Myristica fragrans* that would be effective for increasing perceived focus, mood, energy, and thermogenic effect.

Example 1

The following formulation (F1) was prepared for administration to subjects as capsules containing, per capsule:

| | |
|---|---|
| *Coffea canephora* extract | 400 mg |
| Caffeine anhydrous | 80 mg |
| Raspberry ketone | 50 mg |
| *Myristica fragrans* extract | 50 mg |
| *Salvia officinalis* powder | 50 mg |
| *Ecklonia cava* extract | 18 mg |
| *Pausinystalia yohimbe* extract | 8.5 mg |

Thirteen (13) subjects were given samples and instructed to take 1 or 2 capsules depending on familiarity with, and known tolerance to, caffeine-containing per-workout products. Subjects were asked to rate the formulation on a 10-point scale in terms of: 1) energy, 2) thermogenic effect, 3) focus, and 4) comparison to any favorite thermogenic product.

Eight (8) subjects rated F1 better than their favorite thermogenic product, two (2) rate it equivalent, and three (3) rated it less favorable. Overall ratings in energy, thermogenic effect, and focus were favorable with 5/13 (38%) of the subjects preferring a stronger sensory effect, the remaining 8/13 (62%) of the subjects feeling that the effects were adequate. Based on subject feedback, it was thought that a single capsule of F1 would be recommended for those individuals not familiar with, or those sensitive to, stimulants, particularly caffeine; while for those individuals that regularly use stimulants, particularly caffeine, increasing the amount of *Myristica fragrans* extract may provide additional efficacy.

Example 2

Formulation F2 was prepared similar to F1 above with an increase in the amount of Myristica fragrans as follows containing, per capsule:

| | |
|---|---|
| *Coffea canephora* extract | 400 mg |
| Caffeine anhydrous | 80 mg |
| Raspberry ketone | 50 mg |
| *Myristica fragrans* extract | 100 mg |
| *Salvia officinalis* powder | 50 mg |
| *Ecklonia cava* extract | 18 mg |
| *Pausinystalia yohimbe* extract | 8.5 mg |

Twelve (12) subjects were given F2 as in Example 1 above. With the increase in *Myristica fragrans* extract, 4/12 (33%) of the subjects desired a stronger sensory effect, while 8/12 (67%) of the subjects thought the effects were adequate. Overall feedback from subjects was encouraging in terms of energy and focus, however the inventors believed, based on subject comments, that increasing the amount of caffeine and *Myristica fragrans* extract both may yield a more efficacious composition with respect to energy and the sensory perception of the energy component.

Example 3

The inventors sought to compare the efficacy of a *Myristica fragrans* extract composition containing caffeine to caffeine alone. As caffeine is one of the most used ingredients in both pre-workout nutritional supplements and in weight loss nutritional supplements caffeine was administered to subjects as a baseline for comparisons. The following formulation MCS was prepared, containing per capsule:

| | |
|---|---|
| *Myristica fragrans* extract | 150 mg |
| Caffeine anhydrous | 120 mg |
| *Salvia officinalis* powder | 75 mg |

MCS was compared to caffeine alone (C, 120mg caffeine anhydrous) in ten (10) subjects. The focus and mood effects of MCS was preferred by 6/10 subjects. While more subjects preferred the MCS combination formulation in terms of focus and mood, some component(s) of *Myristica fragrans* and/or *Salvia officinalis* appeared to be buffering the energy and sensory stimulus of caffeine. The inventors theorized that a low dose of yohimbe could support or maintain the sensory/mood effects of *Myristica fragrans* extract combined with caffeine.

Example 4

Formulation F3 was prepared similar to F2 above with an increase in the amount of caffeine and Myristica fragrans as follows:

| | |
|---|---|
| *Coffea canephora* extract | 400 mg |
| Caffeine anhydrous | 120 mg |
| Raspberry ketone | 50 mg |
| *Myristica fragrans* extract | 150 mg |
| *Salvia officinalis* powder | 75 mg |
| *Ecklonia cava* extract | 18 mg |
| *Pausinystalia yohimbe* extract | 8.5 mg |

Eleven (11) subjects were given F3 as in Example 1 above. With the increase in caffeine and *Myristica fragrans* extract, 4/11 (36%) of the subjects desired a stronger sensory effect, while 7/11 (64%) of the subjects thought the effects were adequate.

Example 5

Formulation F4 was prepared similar to F3 above with an increase in the amount of caffeine in order to examine if the benefits of the formulation in terms of energy, focus, and/or thermogenic effect could be further improved without any undesirable effects. as follows containing, per capsule:

| | |
|---|---|
| *Coffea canephora* extract | 400 mg |
| Caffeine anhydrous | 135 mg |
| Raspberry ketone | 50 mg |
| *Myristica fragrans* extract | 100 mg |
| *Salvia officinalis* powder | 75 mg |
| *Ecklonia cava* extract | 18 mg |
| *Pausinystalia yohimbe* extract | 8.5 mg |

Three (3) subjects consumed two capsules of F4. One subject preferred F3 in terms of perceived energy, however F4 was still preferred over caffeine alone (120mg caffeine per capsule); the other two subjects felt the increased caffeine resulted in no difference in terms of energy or thermogenic effect compared to F3 noting a slight improvement in focus but an overall improvement over caffeine alone.

Example 6

A formulation may be prepared similar to those above containing, per capsule:

| | |
|---|---|
| *Coffea canephora* extract | 400 mg |
| Caffeine anhydrous | 135 mg |
| Raspberry ketone | 50 mg |
| *Myristica fragrans* extract | 100 mg |
| *Salvia officinalis* powder | 75 mg |
| *Ecklonia cava* extract | 36 mg |
| *Pausinystalia yohimbe* extract | 8.5 mg |

Overall, there is a perceived increase of at least one of energy, thermogenic effect, focus, and mood in many subjects consuming the compositions. Without wishing to be bound by a particular mechanism, the perceived benefits may be due to independent effects of *Myristica fragrans* (or one or more components thereof) or may be supportive or permissive to the effects of additional ingredients, particularly caffeine. Many subjects accustomed to caffeine reported improved caffeine-related effects while lacking expected negative effects such as crash and jitters encountered at regular or increased dosages of caffeine.

Regarding compositions containing stimulants, for individuals accustomed to pre-workout supplements or weight loss supplements that contain stimulants, particularly caffeine, it would be recommended to take two servings per day. In the case of a pre-workout, one serving would be taken prior to exercise, preferably 60 minutes to 30 minutes prior to exercise. For individuals unaccustomed to supplements containing stimulants, particularly caffeine, it would be recommended to initially take one-half to one serving to assess tolerance, gradually increasing to the recommended dosage as comfortable. Regarding compositions for promoting weight loss, servings should be consumed early in the day, preferably before meals.

The above-described embodiments are intended to be examples of the present invention and alterations and modifications may be effected thereto, by those of skill in the art. The scope of the claims should not be limited by the preferred embodiments set forth in the examples, but should be given the broadest interpretation consistent with the description as a whole.

What is claimed is:

1. A method for improving the efficacy of a composition administered prior to the commencement of exercise for improving exercise performance, the method comprising administering to an individual a composition comprising from 50 to 150 mg of an extract of *Myristica fragrans*, which extract comprises about 10 ug to 10 mg of myristicin, an extract of *Coffea canephora* extract, caffeine anhydrous, raspberry ketone, *Salvia officinalis* powder, an extract of *Ecklonia cava*, and an extract of *Pausinystalia yohimbe*, prior to commencement of exercise.

2. The method of claim 1, wherein the composition is taken by the individual between about 60 minutes to about 30 minutes before commencement of exercise.

3. The method of claim 1, wherein the composition comprises 50 mg of an extract of *Myristica fragrans*, 400 mg of *Coffea canephora* extract, 80 mg of caffeine anhydrous, 50 mg of raspberry ketone, 50 mg of *Salvia officinalis* powder, 18 mg of *Ecklonia cava* extract, and 8.5 mg of *Pausinystalia yohimbe* extract.

4. The method of claim 3, wherein the improvement is at least one of: an increase in thermogenic response, an increase in energy, and an increase in focus.

5. A method for promoting weight loss in a subject in need thereof, the method comprising: administering to a subject a composition comprising [from 50 to 150 mg of] an extract of *Myristica fragrans*, which extract comprises about 10 ug to 10 mg of myristicin, an extract of *Coffea canephora* extract, caffeine anhydrous, raspberry ketone, *Salvia officinalis* powder, an extract of *Ecklonia cava*, and an extract of *Pausinystalia yohimbe*.

6. The method of claim 5, wherein the composition is taken by the individual between about 60 minutes to about 30 minutes before commencement of exercise.

7. The method of claim 5 or 6, wherein the weight loss is supported by an increase in at least one of: an increase in thermogenic response and an increase in energy.

8. The method of claim 1, wherein the composition comprises from 50 to 150 mg of an extract of *Myristica fragrans*, from 200 to 600 mg of *Coffea canephora* extract, from 80 to 250 mg of caffeine anhydrous, from 25 to 125 mg of raspberry ketone, from 10to 150 mg of *Salvia officinalis* powder, from 7.5to 50 mg of *Ecklonia cava* extract, and from 5 to 20 mg of *Pausinystalia yohimbe* extract.

9. The method of claim 1, wherein the composition comprises 100 mg of an extract of *Myristica fragrans*, 400 mg of *Coffea canephora* extract, 80 mg of caffeine anhydrous, 50 mg of raspberry ketone, 50 mg of *Salvia officinalis* powder, 18 mg of *Ecklonia cava* extract, and 8.5 mg of *Pausinystalia yohimbe* extract.

10. The method of claim 1, wherein the composition comprises 150 mg of an extract of *Myristica fragrans*, 400 mg of *Coffea canephora* extract, 120 mg of caffeine anhydrous, 50 mg of raspberry ketone, 75 mg of *Salvia officinalis* powder, 18 mg of *Ecklonia cava* extract, and 8.5 mg of *Pausinystalia yohimbe* extract.

11. The method of claim 1, wherein the composition comprises 100 mg of an extract of *Myristica fragrans*, 400 mg of *Coffea canephora* extract, 135 mg of caffeine anhydrous, 50 mg of raspberry ketone, 75 mg of *Salvia officinalis* powder, 18 mg of *Ecklonia cava* extract, and 8.5 mg of *Pausinystalia yohimbe* extract.

12. The method of claim 1, wherein the composition comprises 100 mg of an extract of *Myristica fragrans*, 400 mg of *Coffea canephora* extract, 135 mg of caffeine anhydrous, 50 mg of raspberry ketone, 75 mg of *Salvia officinalis* powder, 36 mg of *Ecklonia cava* extract, and 8.5 mg of *Pausinystalia yohimbe* extract.

13. The method of claim 1, wherein the composition comprises 150 mg of an extract of *Myristica fragrans*, 120 mg of caffeine anhydrous, and 75 mg of *Salvia officinalis* powder.

14. The method of claim 1, wherein the composition is in the form of a capsule.

15. The method of claim 5, wherein the composition is in the form of a capsule.

16. The method of claim 8, wherein the composition is in the form of a capsule.

17. The method of claim 9, wherein the composition is in the form of a capsule.

18. The method of claim 10, wherein the composition is in the form of a capsule.

19. The method of claim 11, wherein the composition is in the form of a capsule.

20. The method of claim 12, wherein the composition is in the form of a capsule.

21. The method of claim 13, wherein the composition is in the form of a capsule.

* * * * *